(12) United States Patent
Tegels

(10) Patent No.: US 9,597,065 B2
(45) Date of Patent: Mar. 21, 2017

(54) DETACHABLE SEALING PLUG WITH SAFETY RELEASE MECHANISM AND METHODS

(71) Applicant: ST. JUDE MEDICAL PUERTO RICO LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 427 days.

(21) Appl. No.: 13/773,197

(22) Filed: Feb. 21, 2013

(65) Prior Publication Data

US 2014/0236224 A1  Aug. 21, 2014

(51) Int. Cl.
A61B 17/00 (2006.01)

(52) U.S. Cl.
CPC .. *A61B 17/0057* (2013.01); *A61B 2017/0065* (2013.01); *A61B 2017/00557* (2013.01); *A61B 2017/00654* (2013.01)

(58) Field of Classification Search
CPC ...... A61B 17/0057; A61B 2017/00557; A61B 2017/0065; A61B 2017/00654
See application file for complete search history.

(56) References Cited

U.S. PATENT DOCUMENTS

| 4,890,612 A * | 1/1990 | Kensey | A61B 17/0057 606/213 |
| 2002/0077692 A1 * | 6/2002 | Besselink | A61F 2/86 623/1.12 |
| 2005/0283187 A1 | 12/2005 | Longson | |
| 2010/0211000 A1 * | 8/2010 | Killion et al. | 604/57 |
| 2011/0166595 A1 * | 7/2011 | Vidlund | A61B 17/0057 606/213 |
| 2012/0245517 A1 | 9/2012 | Tegels | |

FOREIGN PATENT DOCUMENTS

| WO | 2010027693 A2 | 3/2010 |
| WO | 2012148745 A1 | 11/2012 |

OTHER PUBLICATIONS

PCT International Search Report for International PCT Application No. PCT/US2013/069600, mailed Jan. 27, 2014.

* cited by examiner

*Primary Examiner* — Gregory Anderson
(74) *Attorney, Agent, or Firm* — Holland & Hart

(57) ABSTRACT

A vascular closure system includes a carrier tube, an expandable anchor, a bioadhesive material, a sealing tip, and a filament. The expandable anchor is mounted to the carrier tube and configured to extend through a vessel puncture to temporarily seal the vessel puncture from within a vessel. The bioadhesive material is disposed outside of the vessel and configured to seal the vessel puncture. The sealing tip is mounted to the carrier tube distal of the expandable anchor. The filament is connected to and extends proximally from the sealing tip. Applying tension in the filament maintains connection of the sealing tip to the carrier tube, and releasing the tension in the filament permits release of the sealing tip within a channel formed in the bioadhesive material upon removal of the anchor through the bioadhesive material to seal the channel.

26 Claims, 14 Drawing Sheets

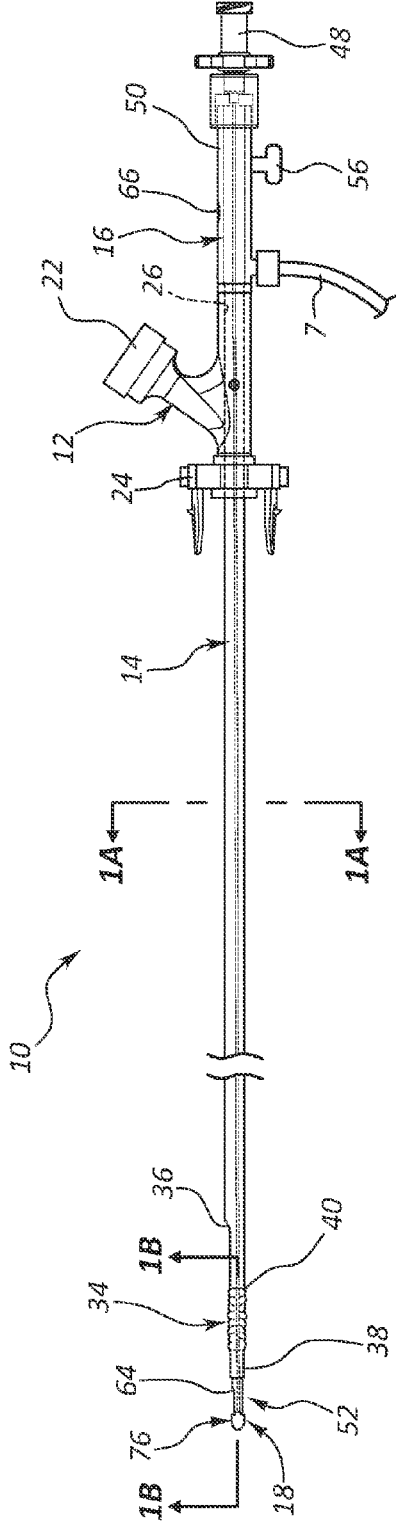

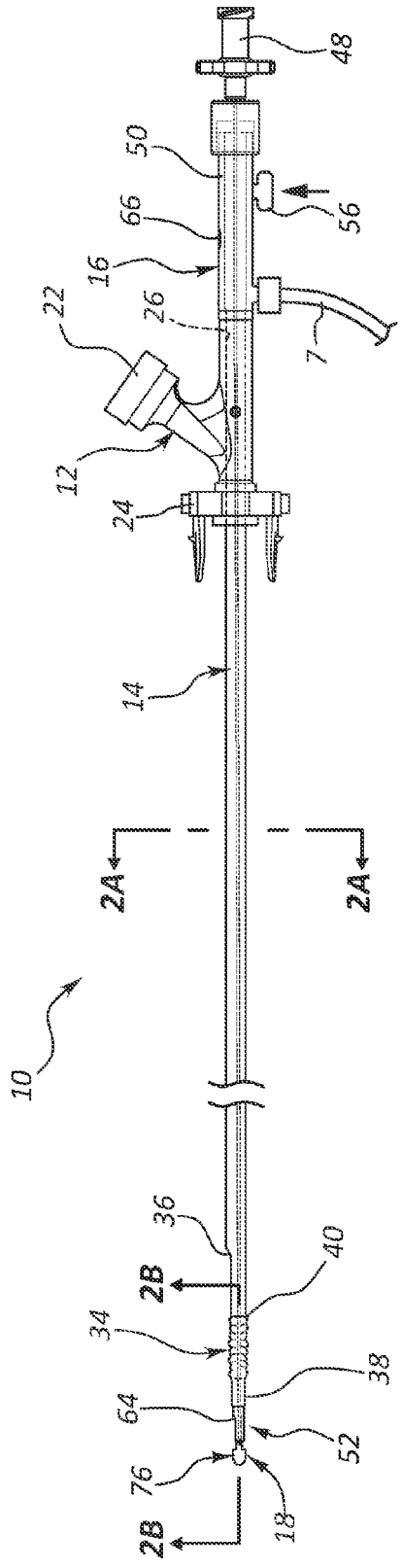
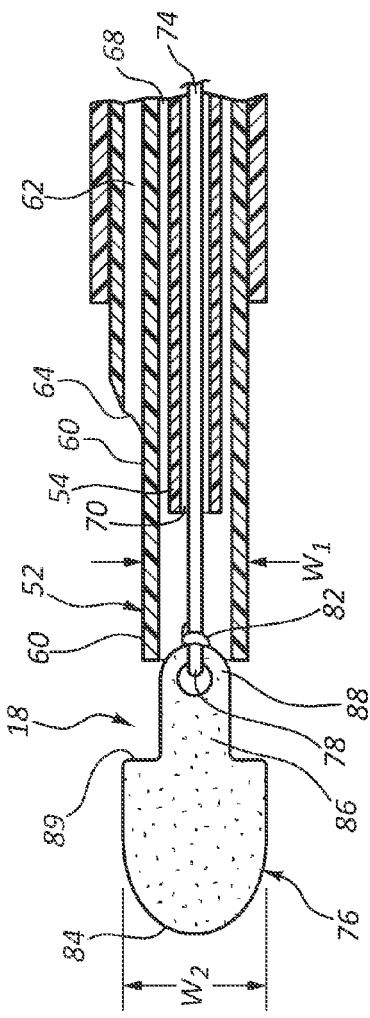
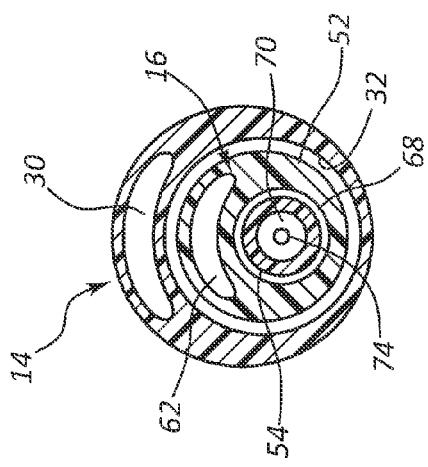
FIG. 2
FIG. 2A
FIG. 2B

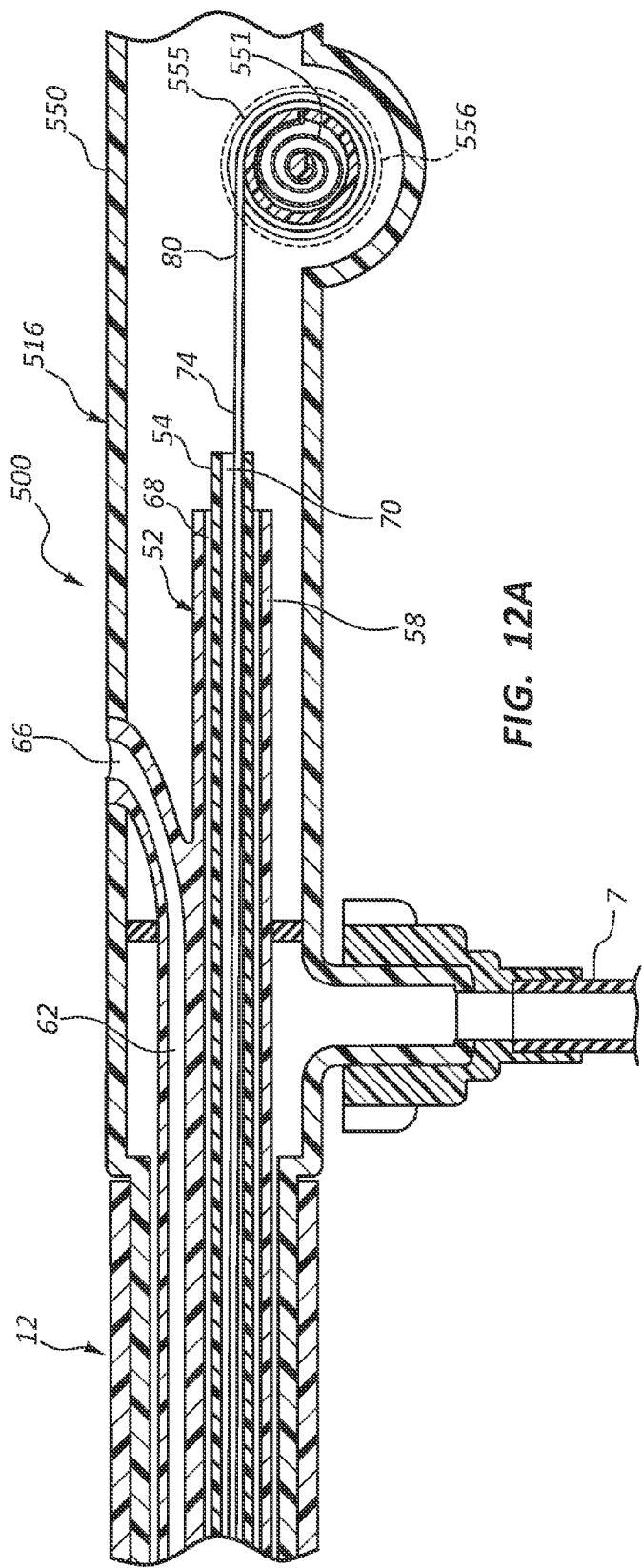
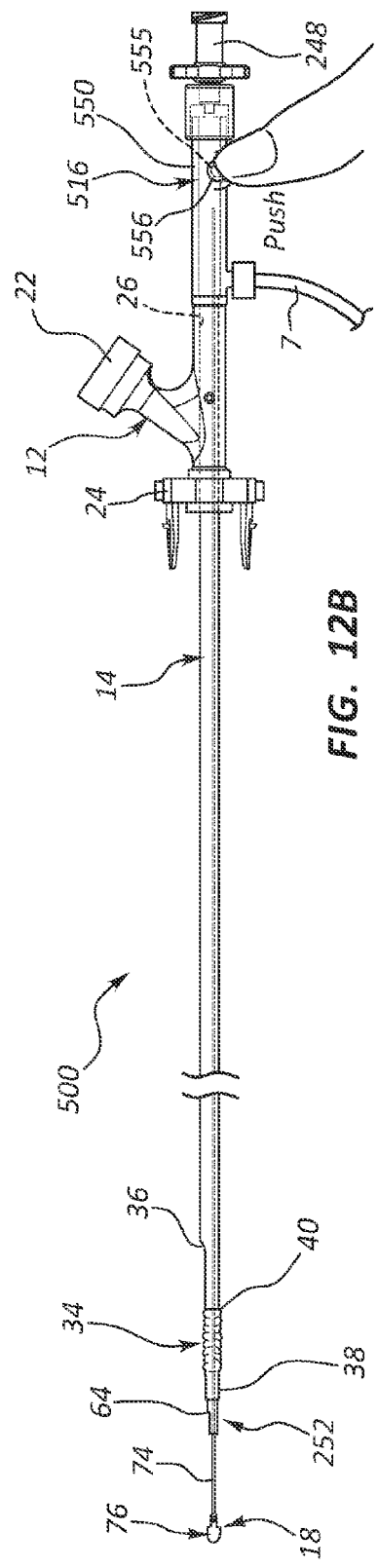
FIG. 12A
FIG. 12B

DETACHABLE SEALING PLUG WITH SAFETY RELEASE MECHANISM AND METHODS

TECHNICAL FIELD

The present disclosure relates generally to methods and systems for sealing tissue punctures, and more particularly, to methods and systems for depositing a secondary sealing member as part of sealing a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while the temporary seal from the balloon is maintained. Removing the collapsed balloon through the sealing material may leave a channel through the sealing material. Challenges exist in closing the channel to provide hemostasis. One way of closing the channel includes depositing a sealing tip within the channel. The sealing tip is susceptible to dislodging and moving into the vessel, wherein the sealing plug could cause a number of problems for the patient. Furthermore, challenges exist in accurately positioning the sealing tip within the sealing material.

SUMMARY

One aspect of the present disclosure relates to a vascular closure system, which includes a carrier tube, an expandable anchor, a bioadhesive material, a sealing tip, and a filament. The expandable anchor is mounted to the carrier tube and configured to extend through a vessel puncture to temporarily seal the vessel puncture from within a vessel. The bioadhesive material is disposed outside of the vessel and configured to seal the vessel puncture. The sealing tip is mounted to the carrier tube at a location distal of the expandable anchor. The filament is connected to and extends proximally from the sealing tip. Applying tension in the filament maintains connection of the sealing tip to the carrier tube, and releasing the tension in the filament permits release of the sealing tip within a channel formed in the bioadhesive material upon removal of the anchor through the bioadhesive material to seal the channel.

The sealing tip may include a maximum width dimension that is greater than a maximum width dimension of the carrier tube. The sealing tip may include a first portion configured to extend into the carrier tube and a second portion extending distal of the carrier tube. The first portion may have a smaller maximum width dimension than a maximum width dimension of the first portion. The sealing tip may include a step feature, and a distal end surface of the carrier tube contacts the step feature. The sealing tip may include an attachment portion, and the filament may be connected to the sealing tip at the attachment portion. The attachment portion may be positioned at a proximal end of the sealing tip. The vascular closure system may also include a cutting member operable to cut the filament to release the tension.

Another aspect of the present disclosure relates to a vascular closure device that includes a bioadhesive delivery device, a balloon location device, and a release mechanism. The bioadhesive delivery device includes at least first and second lumens and is configured to deliver a volume of bioadhesive through the first lumen to a vessel puncture. The balloon location device is insertable through the second lumen and includes an inflation balloon positionable through the vessel puncture and operable to temporarily seal the vessel puncture during delivery of the volume of bioadhesive. The balloon location device also includes a carrier tube extending through the inflation balloon, a detachable sealing tip carried by the carrier tube and positioned distal of the inflation balloon, and a filament connected to the detachable sealing tip and extending through the carrier tube. The filament provides attachment of the detachable sealing tip to the carrier tube. The release mechanism is operable to release the filament to release the detachable sealing tip from the carrier tube and within a channel formed in the volume of bioadhesive upon withdrawal of the vascular closure device from the vessel puncture.

The detachable sealing tip may include a first portion positioned in the carrier tube and connected to the filament, and a second portion extending distally from the carrier tube. The second portion may extend radially beyond an outer circumferential surface of the carrier tube. The detachable sealing tip may include a step feature positioned between the first and second portions, wherein the step feature includes a step surface arranged to abut against a distal end surface of the carrier tube. The release mechanism may include a cutting device configured to sever the filament.

A further aspect of the present disclosure relates to a method of sealing a puncture in a vessel. The method includes providing a vascular closure device having an anchor, a bioadhesive delivery member, and a sealing tip, advancing the anchor and sealing tip through the vessel puncture, expanding the anchor to temporarily seal the vessel puncture from within the vessel, and delivering a volume of bioadhesive to the vessel puncture with the bioadhesive delivery member. The method also includes contracting the anchor, withdrawing the anchor through the volume of bioadhesive, positioning the sealing tip in a channel formed in the volume of bioadhesive upon withdrawal of the anchor, and releasing the sealing tip within the channel to seal the channel.

The sealing tip may include a step feature, and the method may further include contacting a portion of the step feature with the volume of bioadhesive to lodge the sealing tip in the channel. The method may include providing a filament, connecting the filament to the sealing tip, and applying tension in the filament to retain the sealing tip prior to releasing the sealing tip. Releasing the sealing tip may include cutting the filament. Releasing the sealing tip may include releasing the tension in the filament.

The method may include providing a carrier tube extending through the anchor, the sealing tip being mounted at a distal end of the carrier tube, and releasing the sealing tip may include disconnecting the sealing tip from the carrier tube. The method may include positioning a first portion of the sealing tip within the carrier tube and positioning a second portion of the sealing tip extending distally from a distal end of the carrier tube, wherein the second portion extends radially beyond an outer circumferential surface of the carrier tube.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure device in accordance with the present disclosure.

FIG. 1A is a cross-sectional view of the vascular closure device of FIG. 1 taken along cross-section indicators 1A-1A.

FIG. 1B is a cross-sectional view of a distal end portion of the vascular closure device of FIG. 1 taken along cross-section indicators 1B-1B.

FIG. 2 is a side view of the vascular closure device of FIG. 1 with an actuator operated to release a sealing tip of the vascular closure device.

FIG. 2A is a cross-sectional view of the vascular closure device of FIG. 2 taken along cross-section indicators 2A-2A.

FIG. 2B is a cross-sectional view of the distal end portion of the vascular closure device of FIG. 2 taken along cross-section indicators 2B-2B.

FIGS. 12A and 12B show another example suture release mechanism for use with the vascular closure devices disclosed herein.

Throughout the drawings, identical reference numbers designate similar, but not necessarily identical, elements.

DETAILED DESCRIPTION

Figure 1C:
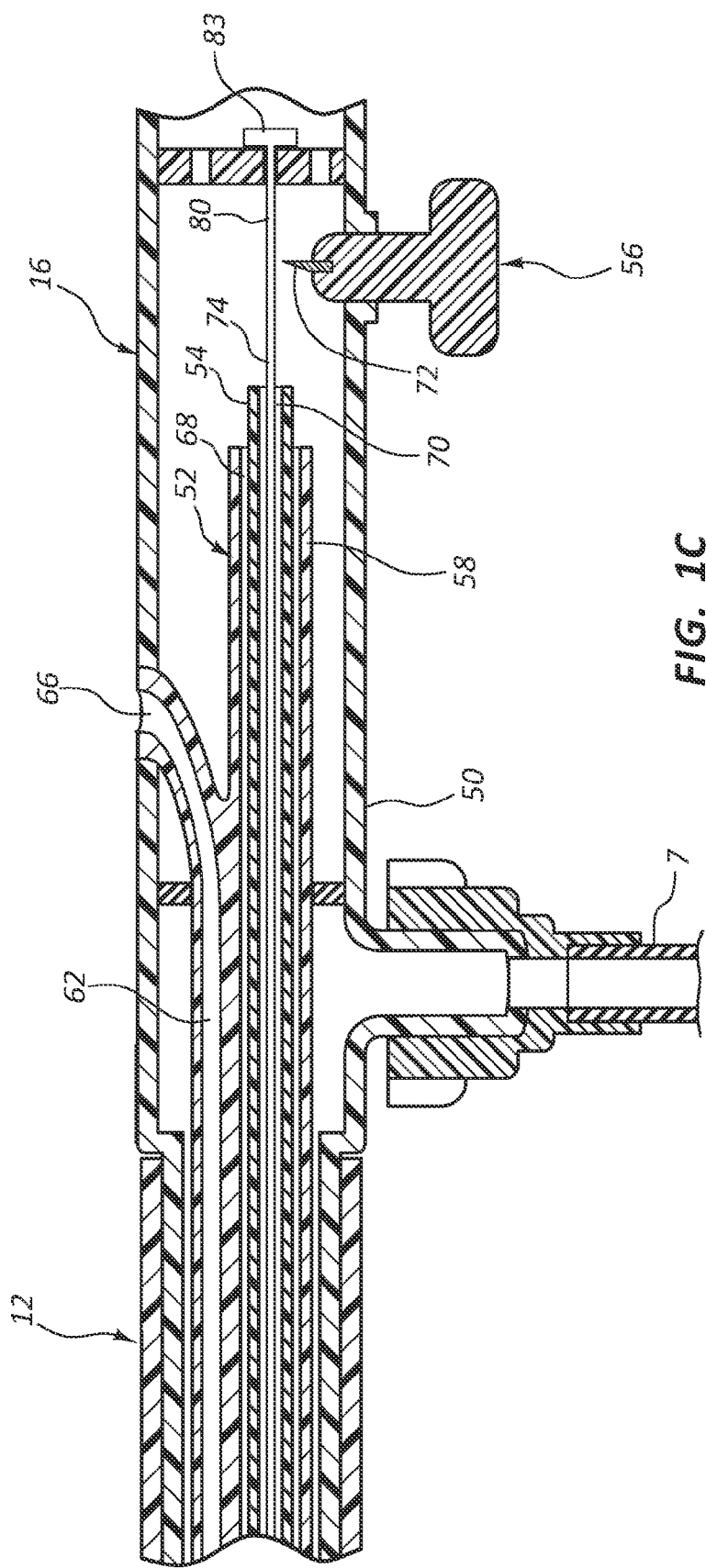
FIG. 1C is a cross-sectional view of a proximal end portion of the vascular closure device of FIG. 1.

The devices and systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems may be applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein may include closure of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An example embodiment of the present disclosure includes a vascular closure device or vascular closure system having a detachable sealing tip. The vascular closure device is used with a sheath that provides access through a vessel puncture and into an inner lumen of the vessel. The vascular closure device may include a delivery tube having a dual lumen construction wherein one lumen is used to deliver a sealing material (e.g., a bioadhesive sealant) to the tissue puncture and the other lumen is used as an inflation lumen for delivering inflation fluid to an inflatable balloon anchor positioned at a distal end of the vascular closure device. The inflation lumen may also be configured for passage of an inner tube (also referred to as a carrier tube) that carries the detachable sealing tip. The inner tube may be part of a balloon location device that temporarily seals the vessel puncture while delivering the bioadhesive. The inner tube may include a separate blood flashback lumen.

The inner tube may also be used to deliver a secondary sealing material (e.g., bioadhesive sealant) to the tissue puncture in addition to carrying the detachable sealing tip. The secondary bioadhesive sealant may be used to help seal a channel defined in the first bioadhesive sealant upon removal of the delivery tube from the vessel. A distal end of the inner tube may extend distally of the balloon. A proximal end of the inner tube may extend proximally to the housing of the balloon location device. An inner tube manifold may be mounted to a proximal end of the inner tube to connect the inner tube with a source for the secondary bioadhesive sealant.

The detachable sealing tip may be carried on the inner tube at a position distal of the balloon. The detachable sealing tip may be part of an assembly that includes the detachable sealing tip and a release member. The release member may operate to release the detachable sealing tip within a channel formed in the delivered bioadhesive. In one example, the release member includes a filament (e.g., a suture or wire), which is connected to the detachable sealing tip to maintain attachment of the detachable sealing tip while delivering the bioadhesive material to the vessel puncture. The filament may extend through the inner tube to the detachable sealing tip. The detachable sealing tip may be released by releasing tension in the filament or disconnecting the filament from the detachable sealing tip. The tension may be released by cutting the filament. In another example, the tension is released by unspooling the filament from a spool. In a further example, the filament is coupled to an actuator, and the actuator is mounted to a handle portion of the vascular closure device. Operating the actuator may release tension in the filament by, for example, breaking the filament or disconnecting the filament from an anchoring feature (e.g., an anchor within the housing). The filament may remain attached to the detachable sealing tip after release of the tension and removal of the vascular closure device from the patient. In other arrangements, the filament may be detached from the sealing tip as part of releasing tension in the filament.

Typically, the detachable sealing tip is released within the sealing material upon withdrawal of the vascular closure device from the vessel puncture. Withdrawing the vascular closure device through the sealing material after the sealing material has at least partially cured and after the balloon anchor has been deflated may create a channel in the sealing material. The detachable sealing tip may be deposited in the channel.

Providing a filament connection to the detachable sealing tip may provide an additional safety feature for the vascular closure device. The filament may provide a positive attachment of the detachable sealing tip until the operator wishes to deposit the detachable sealing tip within the channel of the sealing material. The operator may maintain tension in the filament, which holds the detachable sealing tip in connection with a distal end portion of the vascular closure device during positioning of the vascular closure device within the vessel and depositing the sealing material. The tension may also be maintained while withdrawing the vascular closure device into a position in which the detachable sealing tip is positioned within the channel of the sealing material and the position of the detachable sealing tip is confirmed.

The filament may provide an additional beneficial feature by maintaining connection with the detachable sealing tip after the detachable sealing tip has been deposited within the sealing material. The filament may be used to recapture the detachable sealing tip after being deposited if, for example, the detachable sealing tip is improperly positioned or has inadvertently moved axially into the vessel. The filament may be used to completely remove the detachable sealing tip from the patient, or to simply reposition the detachable sealing tip within the channel of the sealing material.

Figure 2C:
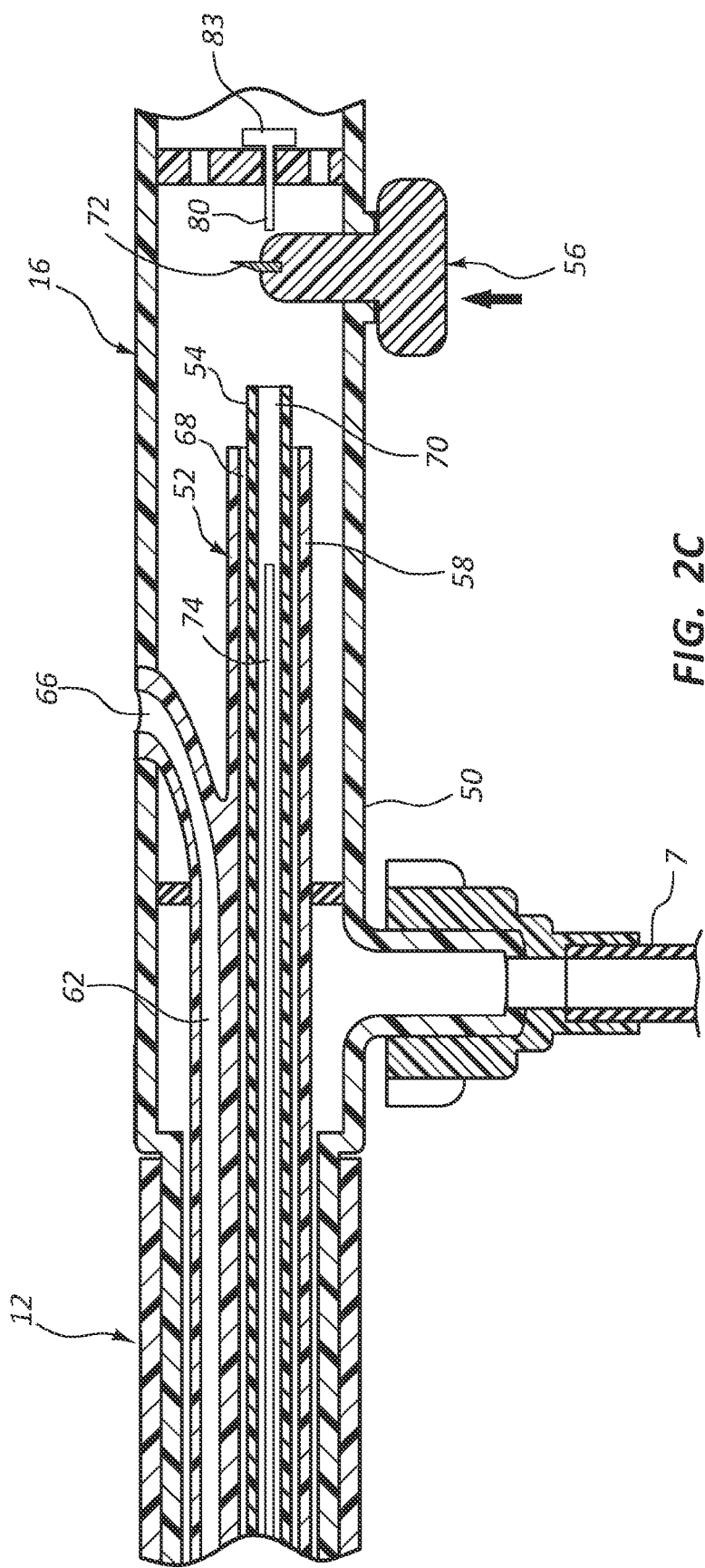
FIG. 2C is a cross-sectional view of the proximal end portion of the vascular closure device of FIG. 2.
Figure 3:
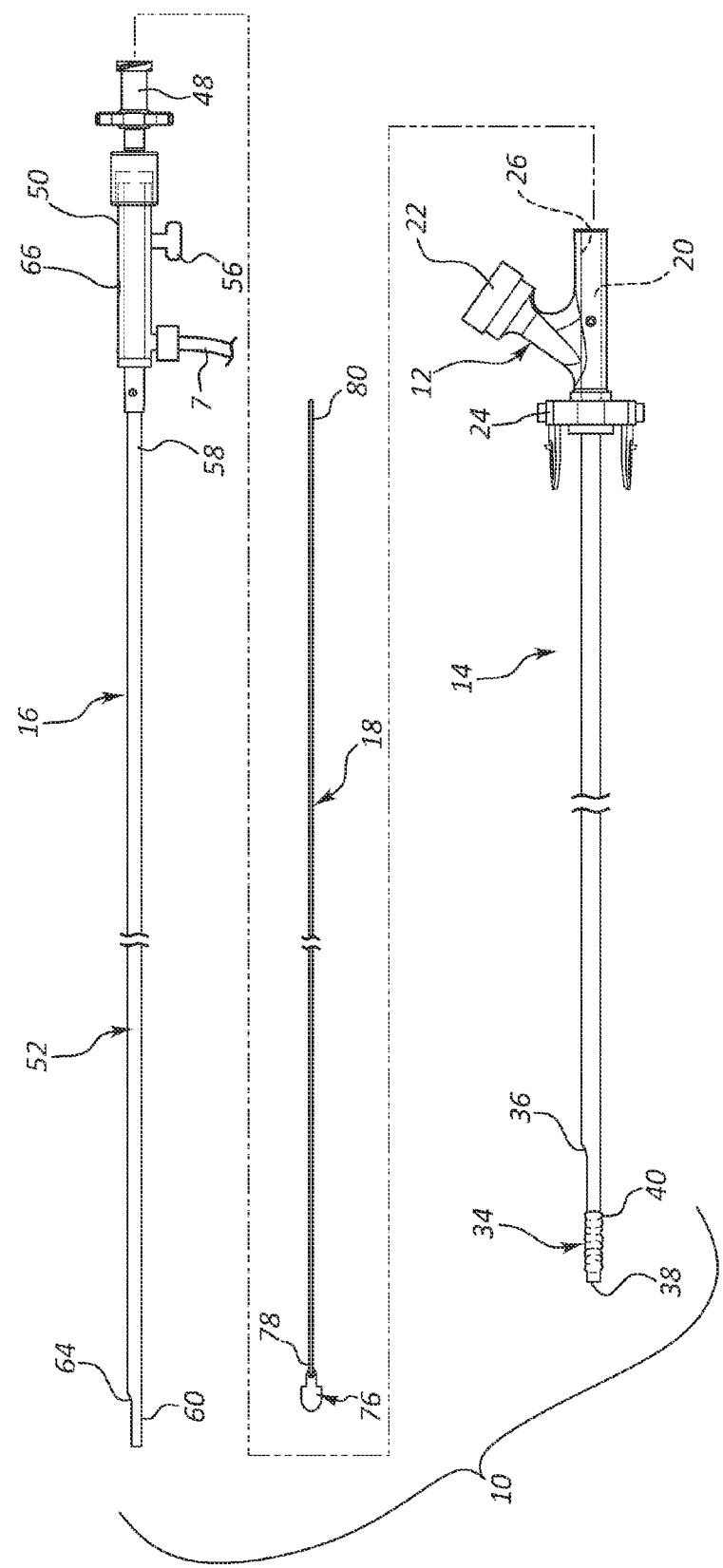
FIG. 3 is an exploded view of the vascular closure device of FIG. 1.
Figure 4:
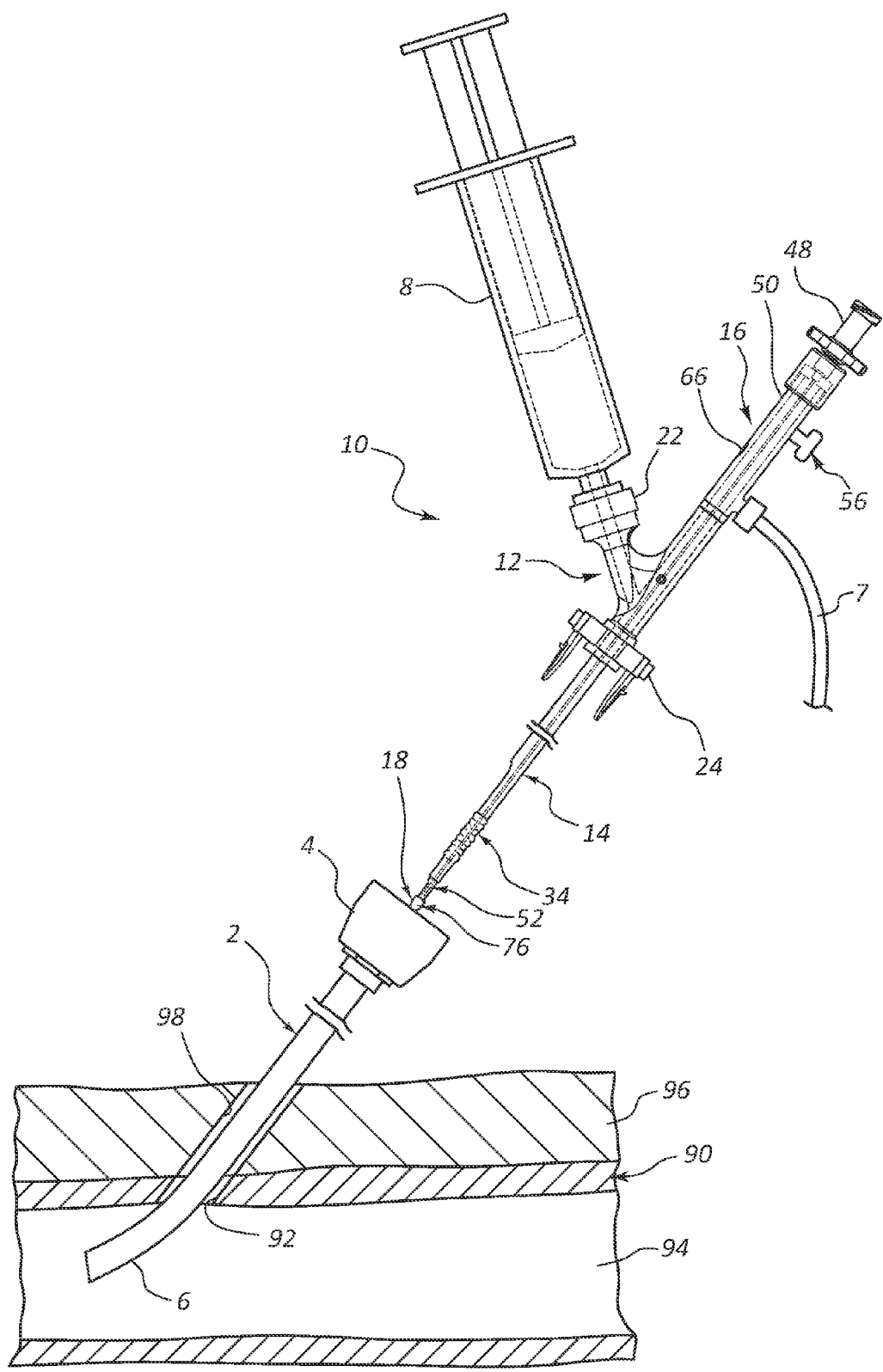
FIGS. 4-9 show the vascular closure device of FIG. 1 in use sealing a vessel puncture in accordance with a method of the present disclosure.

Referring now to FIGS. 1-3, an example vascular closure device 10 is shown and described. The vascular closure device 10 includes a manifold 12, a delivery tube 14, a balloon location device 16, and a detachable sealing tip assembly 18. The vascular closure device may be used with a sheath 2 as shown in FIGS. 4-9 for extravascular treatment of a vessel puncture 92. Operation of vascular closure device 10 may be generally referred to as extravascular closure of vessel puncture 92. Aspects of the vascular closure device 10 may be applicable to other systems and methods of closing openings in a vessel or other tissue.

The delivery tube 14 may extend distally from the manifold 12. The manifold 12 may be connected to a source of sealing material such as a bioadhesive, which is delivered through the delivery tube 14 to the vessel puncture. The balloon location device 16 extends through the manifold 12 and delivery tube 14 to position a balloon at a location distal of the delivery tube 14. The balloon location device 16 may also provide a lumen for positioning of the detachable sealing tip assembly 18 at a distal end of the balloon location device 16. A detachable sealing tip assembly 18 may include a detachable sealing tip 76 and a filament 74 connected to the detachable sealing tip 76, which extends through the balloon location device 16 to a proximal end of the vascular closure device 10. The vascular closure device 10 may include an actuator used to release tension in the filament to detach the detachable sealing tip when depositing a detachable sealing tip within a volume of sealing material, which has been deposited adjacent to the vessel puncture.

The manifold 12 includes a delivery device lumen 20, an injection port 22, and a latch 24 (also referred to as a connector 24). The delivery device lumen 20 includes a proximal seat 26. The injection port 22 is configured to connect to a source of first sealing material. In one example, a first bioadhesive carrier 8 is attached to the injection port 22 as shown in FIGS. 4-8 and provides the first sealing material.

The delivery tube 14 includes first and second lumens 30, 32. The first lumen 30 may be referred to as an inflation lumen coupled to a source of inflation fluid 7, as shown in FIGS. 4-8. The second lumen 32 may be coupled to the injection port 22 for delivery of the sealing material to the vessel puncture. The second lumen 32 may include a distal opening 36 through which the sealing material is ejected adjacent to the vessel puncture.

The delivery tube 14 may support at least a portion of a balloon 34. The balloon 34 may include distal and proximal ends 38, 40. The balloon 34 may be referred to as a expandable member, an anchor, an expandable anchor, an inflation balloon, or an inflatable member. In one example, the proximal end 40 is connected to the delivery tube 14 and the distal end 38 is connected to a shaft or tube of the balloon location device 16. An interior of the balloon 34 may be coupled in flow communication with the first lumen 30.

The balloon location device 16 includes a manifold 48, a housing 50, a carrier tube 52, a hypotube 54, and an actuator 56. The manifold 48 may be connected to the carrier tube 52. The carrier tube 52, which may also be referred to as an inner tube 52, may extend through at least a portion of the housing 50. In some examples, the manifold 48 is coupled in flow communication with at least one lumen of the carrier tube 52. Many arrangements are possible for coupling the manifold 48 to the housing 50 and carrier tube 52 to provide a desired flow path for delivery of, for example, a second volume of bioadhesive to the vessel puncture.

The carrier tube 52 includes proximal and distal ends 58, 60, a flashback lumen 62, and a hypotube lumen 68 receptive of the hypotube 54. The flashback lumen 62 includes distal and proximal openings 64, 66. The distal opening 64 is positioned adjacent to the balloon 34, for example, at a position distal of the balloon 34. The proximal opening 66 is positioned at a proximal end portion of the vascular closure device 10 such as, for example, along the housing 50 as shown in FIG. 1. The flashback lumen 62 may provide a path for blood to flow from the vessel to a location outside of the vessel to provide a visual indicator to the operator that a distal end portion of the vascular closure device is positioned within the vessel. When blood flow through proximal opening 66 stops, the operator has a visual indication that the distal end portion of the vascular closure device is no longer exposed to blood flow in the vessel.

The hypotube lumen 68 may be configured to receive at least a filament 74 of the detachable sealing tip assembly 18. In some arrangements, a separate hypotube 54 is provided and the filament 74 extends through the hypotube. The hypotube lumen 68 may provide a path for the hypotube 54 and the filament 74 of the detachable sealing tip assembly 18 to extend from a proximal end portion of the vascular closure device 10 to its distal end portion. FIG. 1C shows the hypotube 54 terminating within the housing 50. FIG. 1B shows the distal end of the hypotube 54 terminating adjacent to the distal end 60 of the carrier tube 52. The hypotube 54 may have a coating such as, for example, a polymer jacket along its exterior surface. The hypotube 54 may include a lumen 70 through which the filament 74 extends.

The actuator 56 may be mounted to the housing 50. The actuator 56 may include a cutting portion 72 (see FIG. 1C). The cutting portion 72 may move relative to the housing 50 to sever the filament 74. Severing the filament may release tension in the filament 74 and permit detachment of a sealing tip 76 from the carrier tube 52. FIGS. 2-2C show the actuator 56 operated to cut the filament 74 to permit release of the sealing tip 76 from the carrier tube 52. The actuator 56 may be movable radially inward (e.g., in a direction generally perpendicular to a longitudinal axis of the vascular closure device 10). Other arrangements are possible in which the actuator 56 is operated in other direction or in other ways (e.g., through a pivotal or rotation motion) to release tension in the filament 74.

The detachable sealing tip assembly 18 includes a filament 74 and a sealing tip 76. The filament 74 includes distal and proximal ends 78, 80. The distal end 78 is connected to the sealing tip 76 using, for example, a knot 82. The proximal end 80 is secured at a proximal portion of the balloon location device 16 such as, for example, within the housing 50. The proximal end 80 is shown anchored within the housing 50 using an anchor 83 (see FIG. 1C). The anchor 83 may help maintain tension in the filament 74, which tension helps retain the sealing tip 76 in connection with the carrier tube 52.

The sealing tip 76 includes distal and proximal portions 84, 86, an attachment portion 88 positioned at the proximal portion 86, and a step feature 89. The distal portion 84 may include, for example, a rounded or contoured shape. The distal portion 84 may define a distal most surface of the vascular closure device 10, wherein the rounded or contoured shape of the distal portion 84 may improve insertability of the vascular closure device 10 through the vessel puncture into the vessel.

The step 89 may be formed between the distal and proximal portions 84, 86 and may include a step or stop surface. The step 89 may provide an abutment surface that abuts against a distal end surface of the carrier tube 52. The step 89 may define a pointed portion that catches within the channel of the deposited sealing material to help fix an axial position of the sealing tip 76 in the channel.

The sealing tip 76 may include a maximum width $W_2$ that is greater than a maximum width $W_1$ of the carrier tube 52 at the distal end 60 (see FIG. 1B). The greater width $W_2$ of the sealing tip 76 may result in a lip, barb, or catch surface of the sealing tip 76 that extends radially outward from an outer surface of the carrier tube 52. This catch surface may provide improved disconnection of the sealing tip 76 from the carrier tube 52 upon releasing tension in the filament 74 by catching or lodging within the channel of the sealing material to fix an axial position of the sealing tip 76 within the channel.

The attachment portion 88 may include, for example, a lateral bore or aperture through which a portion of the filament 74 extends for connection of the filament 74 to the sealing tip 76. The attachment portion 88 may have other shapes, sizes and configurations for use in attaching the filament 74. In some arrangements, the attachment portion 88 may be configured for releasable connection of the filament 74 to the sealing tip 76.

Figure 11A:
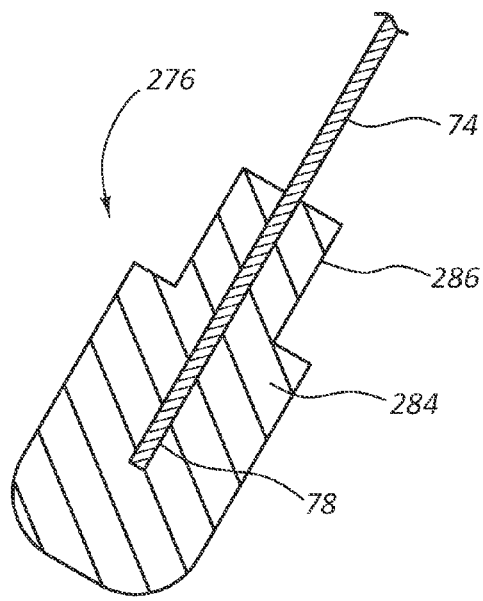
FIGS. 11A-11C are cross-sectional views of further example sealing tips for use with the vascular closure devices disclosed herein.
Figure 11B:
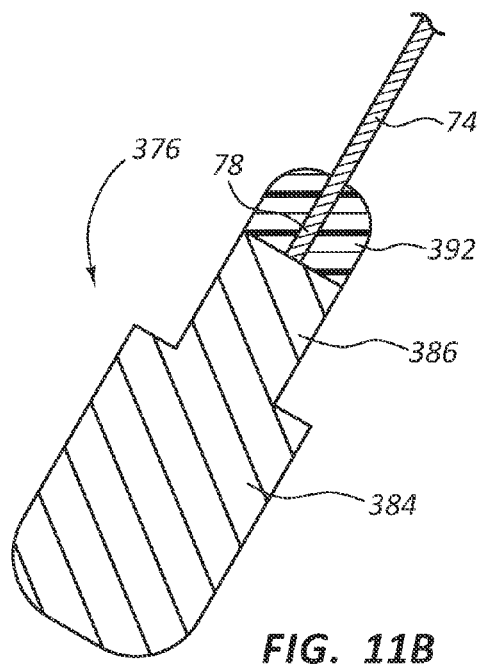
Figure 11C:
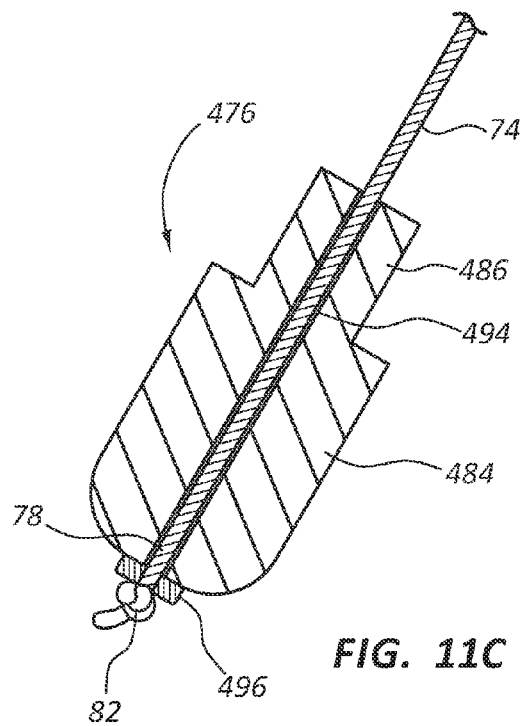

FIGS. 11A-11C show alternative attachment arrangements of the filament 74 to a sealing tip. FIG. 11A shows a sealing tip 276 having a distal portion 284 and a proximal portion 286. A distal end 78 of the filament 74 is embedded within the sealing tip 276. In at least one example, the sealing tip 276 is co-molded over the filament 74. In other examples, the distal end 78 is inserted into a cavity of the sealing tip 276 and secured therein using, for example, an adhesive, clamp, or other securing feature.

FIG. 11B shows another example sealing tip 376 having a distal portion 384 and a proximal portion 386. The filament 74 is connected at its distal end 78 to the sealing tip 376 with a bonding agent 392. The bonding agent 392 may include, for example, an adhesive. The bonding agent 392 may be positioned at a proximal end of the sealing tip 376, for example, at a proximal surface defined by the proximal portion 386. The bonding agent 392 may encapsulate at least a portion of the filament 74. The bonding agent 392 may provide a permanent connection between the filament 74 and the proximal portion 386 of the sealing tip 376. In some arrangements, the bonding agent 392 provides a detachable connection between the filament 74 and the sealing tip 376. For example, the bonding agent 392 may provide release of the filament 74 upon application of a tension force in the filament 74 that exceeds a predetermined level.

FIG. 11C shows a further example sealing tip 476 having a distal portion 484 and a proximal portion 486. The sealing tip 476 includes a channel or bore 494 that extends between distal and proximal end surfaces. A filament 74 extends through the channel 494 and is secured to the sealing tip 476 at a distal end surface thereof. The filament 74 may include a knot 82 having a size and shape that prevents removal of the filament 74 through the channel 494. An additional anchor member 496 may be interposed between the knot 82 and the sealing tip 376 to further limit removal of the filament 74. In other examples, the filament 74 is directly connected to the anchor member 496. The knot 82 and anchor member 496 may be replaced with other connecting features that provide connection of the filament 74 to the sealing tip 476.

Figure 10:
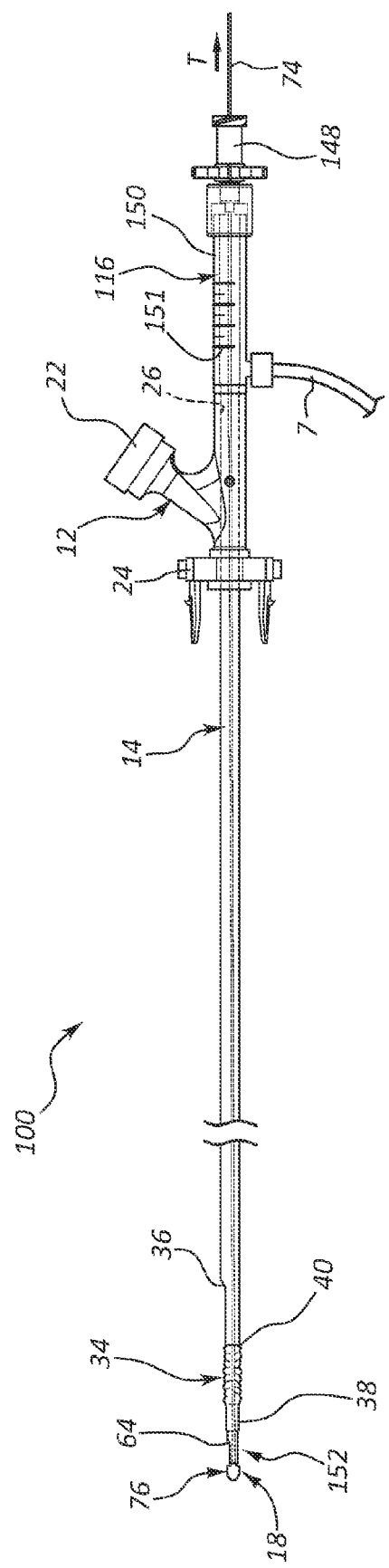
FIG. 10 is a side view of another example vascular closure device in accordance with the present disclosure.

Referring now to FIG. 10, another example vascular closure device 100 is shown including a different arrangement for applying tension to the filament 74. The vascular closure device 100 includes a balloon location device 116. The filament 74 extends completely through a manifold 148 and housing 150 of the balloon location device 116 and is exposed proximally thereof. The operator may apply a tension force T in the filament 74 that maintains connection of the sealing tip 76 to a carrier tube 152 at a distal end thereof. The hypotube of the balloon location device 116 may also extend completely through the housing 150 and may be coupled in flow (e.g., fluid) communication with the manifold 148. Tension in the filament 74 may be maintained in a number of ways including, for example, securing the filament 74 to an anchoring device positioned proximal of the housing 150 or to an exterior of the housing 150 or manifold 148.

The housing 150 may include a plurality of markings 151 on an exterior surface thereof. The markings 151 may provide a visual indicator to the operator of an axial position of the filament 74 relative to the housing 150. The filament 74 may include at least one marking along its length that helps the operator track an axial position of the filament 74 relative to the markings 151. An axial position of the filament 74 may correlate with an axial position of the sealing tip 76 or other features of the vascular closure device 100 at the distal end thereof.

Referring now to FIGS. 4-9, an example method of operating the vascular closure device 10 to seal a vessel puncture 92 is shown and described. The vascular closure device 10 and sheath 2 may extend through a vessel puncture 92 and into a lumen 94 of a vessel 90. The vascular closure device 10 and sheath 2 extend through a tissue tract 98 of a tissue layer 96 to access the vessel puncture 92. The tissue tract 98 may be referred to as a percutaneous incision, and accessing the vessel puncture 92 through the tissue layer 96 may be referred to as accessing a vessel puncture percutaneously.

In a first operational step, a distal end 6 of the sheath 2 is advanced through the tissue tract 98 and vessel puncture 92 and into the vessel lumen 94. The vascular closure device 10 is aligned with an opening into a hub 4 of the sheath 2 for insertion into the sheath 2. Prior to inserting the vascular closure device 10 into the sheath 2, the delivery tube 14 is connected to the manifold 12 and the balloon location device 16 is advanced through the manifold 12 and delivery tube 14 until connected at a proximal end thereof to the manifold 12. The detachable sealing tip assembly 18 is assembled with the vascular closure device 10 with the sealing tip 76 positioned at a distal end thereof and the filament 74 extending proximally to the housing 50 of the balloon location device 16. The actuator 56 is positioned in a removed position relative to the filament 74.

Figure 5:
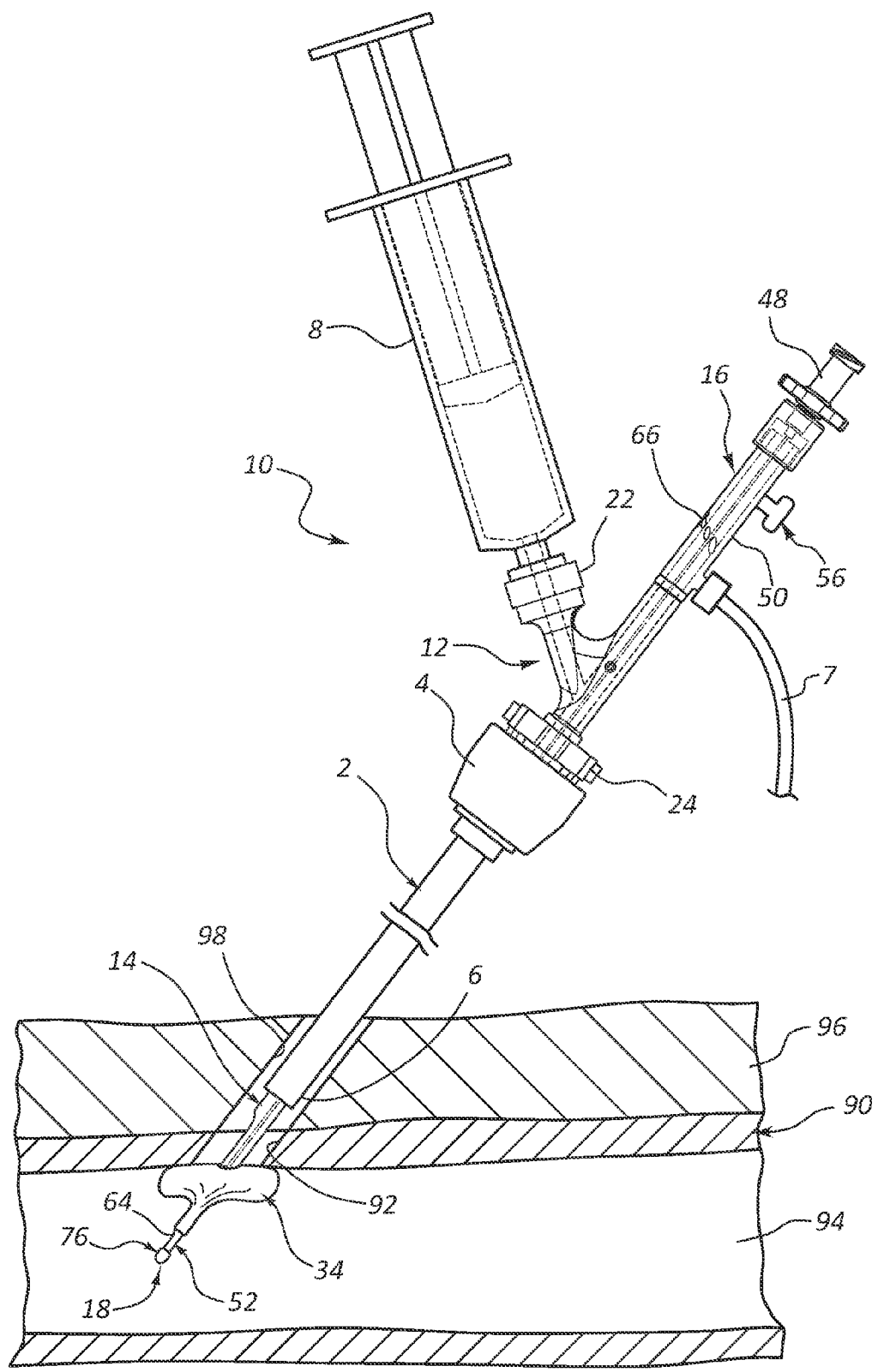

Referring to FIG. 5, the delivery tube 14 is advanced through the sheath 2 and the latch 24 is connected to the hub 4. The vascular closure device 10 and sheath 2 move in tandem after being connected together with the latch 24. The balloon 34 is inflated by delivering a volume of inflation fluid from the source of inflation fluid 7, through the housing 50 of the balloon location device 16, and through the first lumen 30 into the balloon 34. The inflation fluid may flow in a space defined between the second lumen 32 and an outer surface of the carrier tube 52.

The vascular closure device 10 and sheath 2 are refracted (e.g., withdrawn proximally) to bring the balloon 34 into contact with an inner surface of the vessel 90 adjacent to the vessel puncture 92. The inflated balloon 34 may provide a temporary seal with the vessel 90 to limit blood flow through the vessel puncture 92, which may be referred to as hemostasis or temporary hemostasis.

Figure 6:
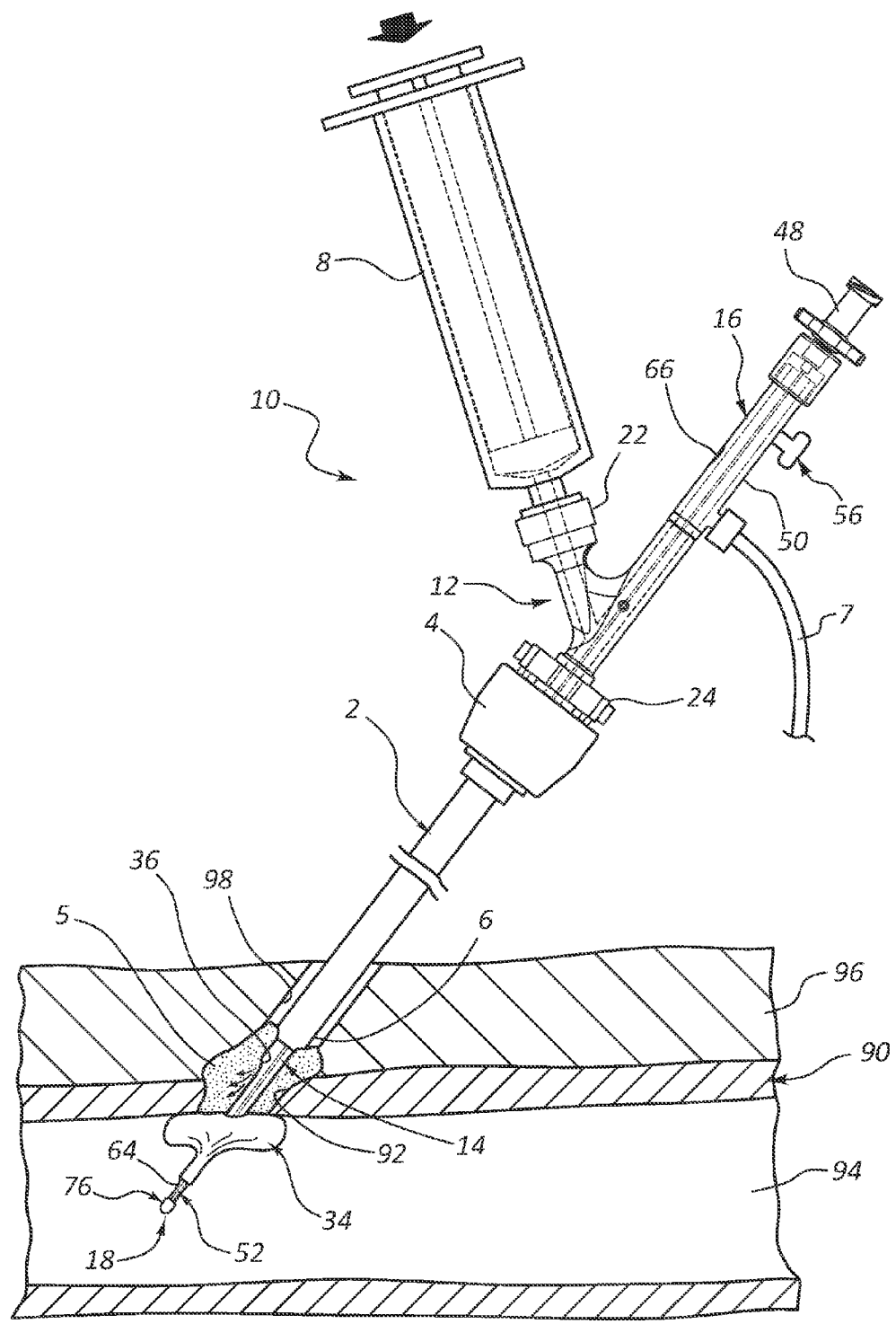

Referring to FIG. 6, a sealing material (e.g., bioadhesive sealant) is delivered to the vessel puncture 92 and tissue tract 98 through the distal opening 36 of the second lumen 32. A source of sealing material may include a bioadhesive carrier 8, which is connected to the injection port 22 of the manifold 12. Operating the bioadhesive carrier 8 delivers a volume of the sealing material through the manifold 12, the second lumen 32, and out of the distal opening 36. The sealing material forms a first bioadhesive plug 5 that seals the vessel puncture 92 and tissue tract 98 from a location outside of the vessel 90. The first bioadhesive plug 5 may be allowed to at least partially cure into a solid or semi solid state. The first bioadhesive plug, when cured, may have a shape and size that limits distal movement of the first bioadhesive plug 5 through the vessel puncture 92 and into the vessel lumen 94 after deflating balloon 34. The amount of time required to at least partially cure the sealing material of the first bioadhesive plug 5 may be in the range of about 5 seconds to about 180 seconds, and more preferably in the range of about 15 seconds to about 30 seconds.

Figure 7:
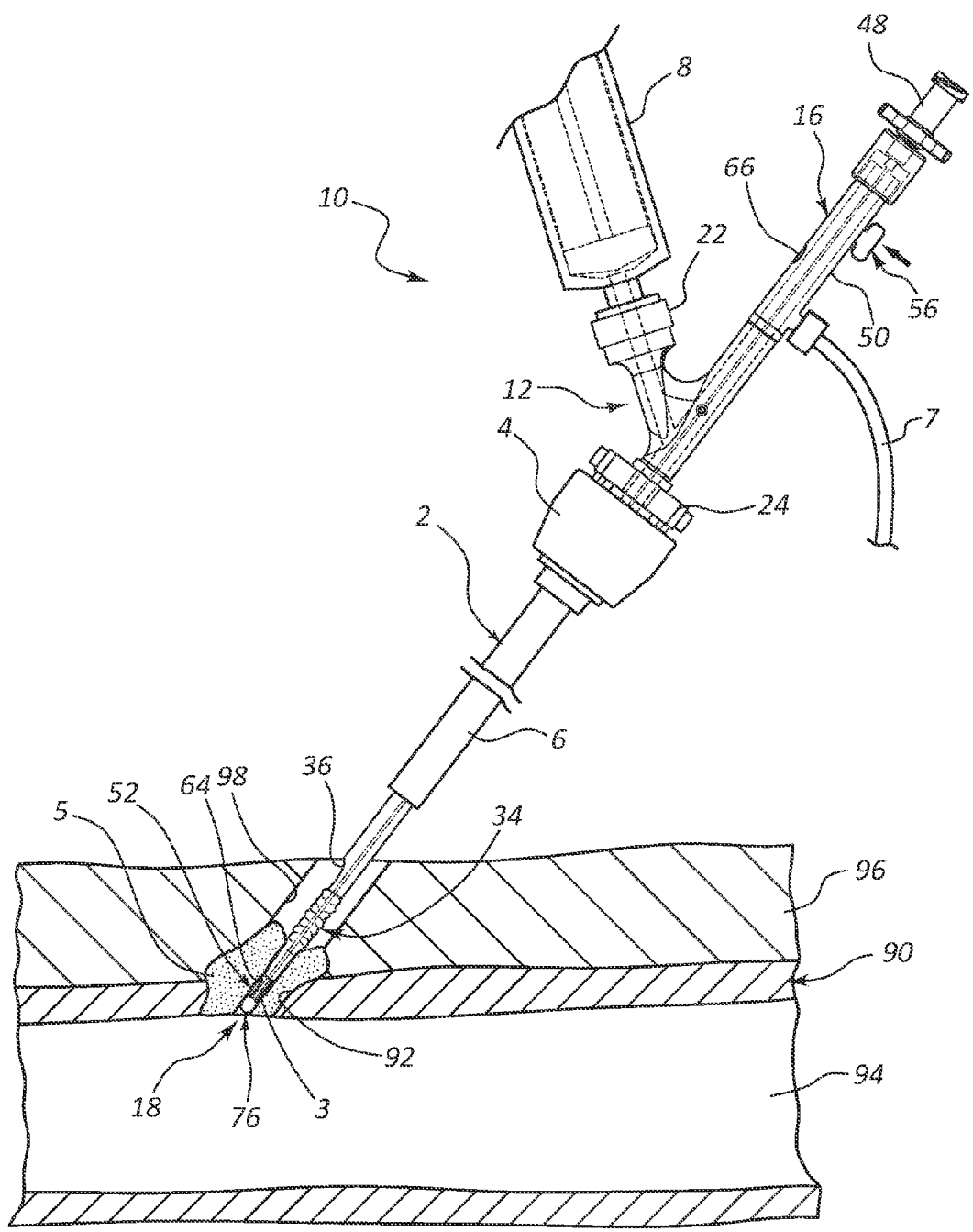

Referring now to FIG. 7, the balloon 34 is deflated by withdrawing the inflation fluid through the first lumen 30, through the balloon location device 16, and into the source of inflation fluid 7. The vascular closure device 10 and sheath 2 are further retracted so that the delivery tube 14 is positioned proximal of the first bioadhesive plug 5. A channel 3 may be defined within the first bioadhesive plug 5 upon removal of the delivery tube 14 and balloon 34. The sealing tip 76 may be positioned within the channel 3. The detachable sealing tip assembly 18 may be operated to deposit the sealing tip 76 within the channel 3. The sealing tip 76 may be released by removing tension in the filament 74. The tension may be released by, for example, operating the actuator 56 to cut the filament 74 with the cutting portion 72 (e.g., see FIGS. 2 and 2B). In other arrangements, the tension in filament 74 may be released by the operator manually letting go of the filament 74 such as in the arrangement of vascular closure device 100 shown in FIG. 10.

Alternatively, the tension is released in filament 74 by operating a release member 556 of a vascular closure device 500 to release a spool 555 about which the filament 74 is wound as part of the balloon location device 516 shown in FIGS. 12A and 12B. The spool 555 is positioned in a housing 550 and the release member 556 may extend through the housing and be coupled to the spool 555. The spool 555 may have a moment force applied thereto by, for example, a coil spring 551 (see FIG. 12A). Tension in the filament may be released by operating a device or performing a function that occurs along an exterior of the vascular closure device for improved ease of operation by the operator. In some arrangements, the tension is released automatically upon exceeding a threshold withdrawal force of, for example, the balloon location device 16 relative to the manifold 12 or delivery tube 14. For example, the sealing tip 76 (i.e., the lip formed by step 89) may contact an end surface of the delivery tube 14 or the sheath 2, and further withdrawal of the balloon location device 16 (e.g., by application of a withdrawal force to housing 50) may exceed a threshold tension in the filament 74, which causes the filament 74 to break or provides detachment of the filament 74 from the sealing tip 76.

In another example, exceeding the threshold tension force may automatically cause the spool 555 of the balloon location device 516 shown in FIGS. 12A and 12B to unwind, or the anchor 83 shown in FIG. 1C to release from housing 50.

Figure 8:
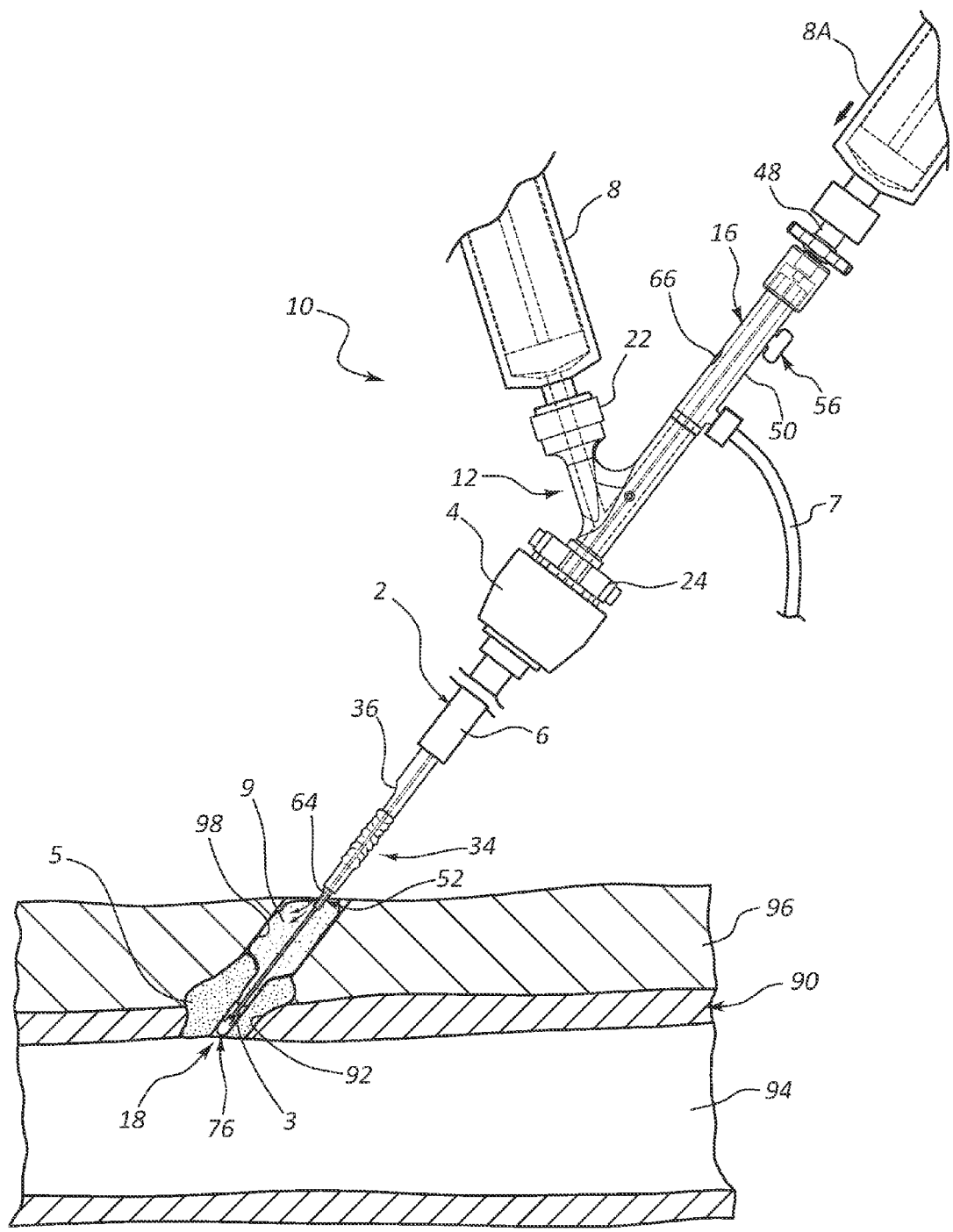

After the tension is released in the filament 74 as shown in FIG. 7, the sealing tip 76 maintains its position within channel 3 and the remaining portions of the vascular closure device 10 are further withdrawn as shown in FIG. 8. A second volume of sealing material may be advanced into the tissue tract 98 to further seal the vessel puncture 92, tissue tract 98 and channel 3. In one example, the second volume of sealing material is delivered through the carrier tube 52. A source of second sealing material 8A may be connected in flow communication with, for example, the manifold 48. The second volume of bioadhesive may flow through, for example, the hypotube lumen 68, or the lumen 70 of hypotube 54. The second volume of sealing material may form a second bioadhesive plug 9. At least portions of the second sealing material may flow into channel 3 to further seal channel 3. The second volume of sealing material may contact the sealing tip 76 to provide a connection with the sealing tip 76, which may further secure the sealing tip 76 from being able to advance distally into the vessel lumen 94.

Figure 9:
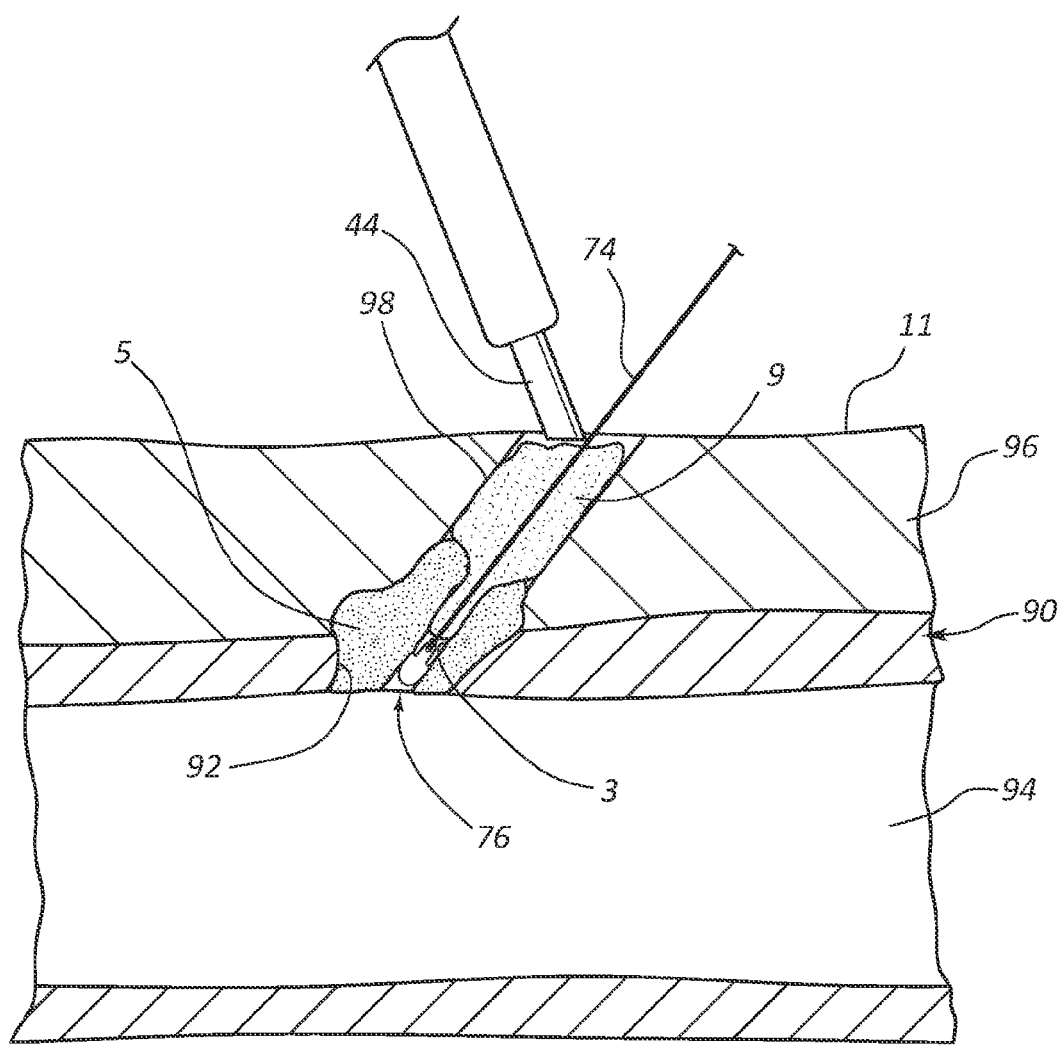

FIG. 9 shows the vascular closure device 10 removed and the first and second bioadhesive plugs 5, 9 positioned within the tissue tract 98 to seal the vessel puncture 92. The operator might perform an additional step of cutting the filament 74 at a location below an outer surface 11 of the patient. The filament 74 may be cut using, for example, a cutting device 44. A distal tip of the cutting device 44 may extend into the tissue tract 98 to cut the filament 74 below the outer surface 11. As shown in FIG. 9, the filament 74 may be cut with a portion configured to extend outside of the second bioadhesive plug 9 and the channel extending through the plug 9. In some examples, the cutting device 44 may cut the filament 74 within the second bioadhesive plug 9.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure system, comprising:
   a carrier tube;
   an expandable anchor mounted to the carrier tube and configured to extend through a vessel puncture to temporarily seal the vessel puncture from within a vessel;
   a first lumen positioned in the carrier tube and a second lumen positioned in the carrier tube, the first and second lumens having distal openings positioned distal to the expandable member;
   a bioadhesive material disposed outside of the vessel and configured to seal the vessel puncture;
   a sealing tip mounted to the carrier tube distal of the expandable anchor;
   a filament connected to and extending proximally from the sealing tip, wherein applying tension in the filament maintains connection of the sealing tip to the carrier tube, and releasing the tension in the filament permits release of the sealing tip and at least a portion of the filament within a channel formed in the bioadhesive material upon removal of the anchor through the bioadhesive material to seal the channel, the filament being movable through the expandable anchor, wherein the at least a portion of the filament is configured to extend outside of the bioadhesive material upon removal of the anchor.

2. A vascular closure system according to claim 1, wherein the sealing tip includes a maximum width dimension that is greater than a maximum width dimension of the carrier tube.

3. A vascular closure system according to claim 1, wherein the sealing tip includes a first portion configured to extend into the carrier tube and a second portion extending distal of the carrier tube.

4. A vascular closure system according to claim 3, wherein the first portion has a smaller maximum width dimension than a maximum width dimension of the first portion.

5. A vascular closure system according to claim 1, wherein the sealing tip includes a step feature, and a distal end surface of the carrier tube contacts the step feature.

6. A vascular closure system according to claim 1, wherein the sealing tip comprises an attachment portion, the filament being connected to the sealing tip at the attachment portion.

7. A vascular closure system according to claim 6, wherein the attachment portion is positioned at a proximal end of the sealing tip.

8. A vascular closure system according to claim 1, further comprising a cutting member operable to cut the filament to release the tension.

9. The vascular closure system of claim 1, further comprising a housing, the housing comprising a housing marking, the filament comprising a filament marking, wherein relative positions of the housing marking and the filament marking indicate an axial position of the filament relative to the housing.

10. The vascular closure system of claim 1, wherein the sealing tip comprises a bore through the sealing tip, the filament extending through the bore.

11. A vascular closure device, comprising:
    a bioadhesive delivery device having at least first and second lumens and configured to deliver a volume of bioadhesive through the first lumen to a vessel puncture;
    a balloon location device insertable through the second lumen and comprising:
       an inflation balloon positionable through the vessel puncture and operable to temporarily seal the vessel puncture during delivery of the volume of bioadhesive;
       a carrier tube extending through the inflation balloon;
       a first location device lumen extending through the carrier tube and a second location device lumen extending through the carrier tube, the first and second location device lumens each having distal openings positioned distal to the inflation balloon;
       a detachable sealing tip carried by the carrier tube and positioned distal of the inflation balloon;
       a filament connected to the detachable sealing tip and extending through the carrier tube, the filament attaching the detachable sealing tip to the carrier tube, the filament being movable through the inflation balloon;
       an anchor positioned on a proximal end of the filament;
    a release mechanism operable to release the filament by cutting the filament proximate to the anchor to release a portion of the filament and the detachable sealing tip from the carrier tube with the portion of the filament and the detachable sealing tip remaining within a channel formed in the volume of bioadhesive upon withdrawal of the vascular closure device from the vessel puncture, wherein the release mechanism is configured to cut the filament to a length partially extending outside of the volume of bioadhesive.

12. A vascular closure device according to claim 11, wherein the detachable sealing tip includes a first portion positioned in the carrier tube and being connected to the filament, and a second portion extending distally from the carrier tube.

13. A vascular closure device according to claim 12, wherein the second portion extends radially beyond an outer circumferential surface of the carrier tube.

14. A vascular closure device according to claim 12, wherein the detachable sealing tip comprises a step feature between the first and second portions, the step feature including a step surface arranged to abut against a distal end surface of the carrier tube.

15. A vascular closure device according to claim 11, wherein the release mechanism comprises a cutting device configured to sever the filament.

16. The vascular closure device of claim 11, further comprising a housing, the housing comprising a housing marking, the filament comprising a filament marking, wherein relative positions of the housing marking and the filament marking indicate an axial position of the filament relative to the housing.

17. The vascular closure device of claim 11, wherein the filament is connected to the detachable sealing tip by extending through a bore in the detachable sealing tip.

18. A method of sealing a vessel puncture in a vessel, comprising:
providing a vascular closure device having an anchor, a first lumen, a second lumen, a bioadhesive delivery member, a filament, and a sealing tip;
advancing the anchor and sealing tip through the vessel puncture with distal openings of the first and second lumens being positioned distal to the anchor;
expanding the anchor to temporarily seal the vessel puncture from within the vessel;
delivering a volume of bioadhesive to the vessel puncture with the bioadhesive delivery member;
contracting the anchor and withdrawing the anchor through the volume of bioadhesive, wherein the anchor moves relative to the filament;
positioning the sealing tip and a portion of the filament in a channel formed in the volume of bioadhesive upon withdrawing the anchor;
releasing the sealing tip and the portion of the filament within the channel to seal the channel with the filament partially extending outside of the channel.

19. A method according to claim 18, wherein the sealing tip comprises a step feature, the method further comprising contacting a portion of the step feature with the volume of bioadhesive to lodge the sealing tip in the channel.

20. A method according to claim 18, further comprising providing a filament, connecting the filament to the sealing tip and applying tension in the filament to retain the sealing tip prior to releasing the sealing tip.

21. A method according to claim 20, wherein releasing the sealing tip includes cutting the filament.

22. A method according to claim 20, wherein releasing the sealing tip includes releasing the tension in the filament.

23. A method according to claim 18, further comprising providing a carrier tube extending through the anchor, the sealing tip being mounted at a distal end of the carrier tube, and releasing the sealing tip includes disconnecting the sealing tip from the carrier tube.

24. A method according to claim 23, further comprising positioning a first portion of the sealing tip within the carrier tube and positioning a second portion of the sealing tip extending distally from a distal end of the carrier tube, the second portion extending radially beyond an outer circumferential surface of the carrier tube.

25. The method of claim 18, wherein the vascular closure device comprises a housing having a housing marking and wherein the filament comprises a filament marking, the method further comprising comparing the housing marking and the filament marking to determine an axial position of the filament relative to the housing.

26. The method of claim 18, further comprising positioning the filament through a bore in the sealing tip.

* * * * *